(12) United States Patent
Bürger et al.

(10) Patent No.: US 8,467,587 B2
(45) Date of Patent: Jun. 18, 2013

(54) METHOD FOR DISTINGUISHING BETWEEN GRAY MATTER AND WHITE MATTER AND CT SYSTEM FOR CARRYING OUT THE METHOD

(75) Inventors: Corinna Bürger, Erlangen (DE); Ernst Klotz, Uttenreuth (DE); Jochen Schleu, Erlangen (DE); Grzegorz Soza, Nürnberg (DE)

(73) Assignee: Siemens Aktiengesellschaft, Munich (DE)

( * ) Notice: Subject to any disclaimer, the term of this patent is extended or adjusted under 35 U.S.C. 154(b) by 808 days.

(21) Appl. No.: 12/641,452

(22) Filed: Dec. 18, 2009

(65) Prior Publication Data
US 2010/0166281 A1    Jul. 1, 2010

(30) Foreign Application Priority Data

Dec. 22, 2008  (EP) .................................... 08022295
Sep. 18, 2009  (DE) .......................... 10 2009 042 129

(51) Int. Cl.
*G06K 9/00*    (2006.01)
(52) U.S. Cl.
USPC ........................... 382/131; 382/128; 382/130
(58) Field of Classification Search
USPC ................. 382/128, 130, 131; 378/4, 5, 98.9
See application file for complete search history.

(56) References Cited

U.S. PATENT DOCUMENTS

| | | | | |
|---|---|---|---|---|
| 4,856,528 A | * | 8/1989 | Yang et al. | 382/131 |
| 5,024,230 A | * | 6/1991 | Lindstrom et al. | 600/431 |
| 5,042,077 A | * | 8/1991 | Burke | 382/169 |
| 5,761,333 A | * | 6/1998 | Hsieh et al. | 382/131 |
| 6,138,045 A | * | 10/2000 | Kupinski et al. | 600/425 |
| 6,310,967 B1 | * | 10/2001 | Heine et al. | 382/128 |
| 6,754,274 B2 | * | 6/2004 | Park | 375/240.25 |
| 2005/0058331 A1 | | 3/2005 | Klotz | |
| 2007/0248265 A1 | * | 10/2007 | Lundstrom et al. | 382/168 |
| 2008/0221441 A1 | * | 9/2008 | Bjornerud et al. | 600/425 |
| 2008/0247503 A1 | * | 10/2008 | Lauritsch et al. | 378/4 |

FOREIGN PATENT DOCUMENTS

DE     10335663     3/2005

OTHER PUBLICATIONS

Office Action for German patent application No. 10 2009 042 129.7 dated Jun. 9, 2011.

* cited by examiner

*Primary Examiner* — Alexander H Taningco
(74) *Attorney, Agent, or Firm* — Harness, Dickey & Pierce, P.L.C.

(57) ABSTRACT

A method for distinguishing between gray matter and white matter starting from a time-dependent computed tomography image data record from a perfusion CT examination is disclosed. In at least one embodiment, a plurality of time-independent images are calculated from the time-dependent image data record, a plurality of threshold histogram analyses are performed in order to determine regions of the brain which can be assigned to one or more types of cerebral matter, and subsequently the region of gray matter is determined from the information obtained in respect of type and region of the cerebral matter using at least one logical combination and at least one exclusion method. A control and computational unit is also disclosed with a storage medium in which a computer program or program module is stored, which executes the described method during operation.

28 Claims, 2 Drawing Sheets

METHOD FOR DISTINGUISHING BETWEEN GRAY MATTER AND WHITE MATTER AND CT SYSTEM FOR CARRYING OUT THE METHOD

PRIORITY STATEMENT

The present application hereby claims priority under 35 U.S.C. §119 on European patent application number EP08022295 filed Dec. 22, 2008 and on German patent application number DE 10 2009 042 129.7 filed Sep. 18, 2009, the entire contents of each of which are hereby incorporated herein by reference.

FIELD

At least one embodiment of the invention generally relates to a method for distinguishing between gray matter and white matter in the hemispheres of a brain, in particular within the scope of an infarct examination, on the basis of a time-dependent computed tomography image data record from a perfusion CT examination, wherein the gray matter can have ischemic cerebral matter and a plurality of known methods are combined and information from a number of image data records is interlinked.

BACKGROUND

Perfusion CT examinations for diagnosing an ischemic stroke are known. This examination method allows a quantitative determination of the brain perfusion and so regions of the brain with insufficient perfusion can be detected directly, and a distinction can be made between the already irreversibly damaged cerebral matter, the infarct core, and the only reversibly damaged cerebral matter, the infarct penumbra.

In order to assess the blood flow in the brain, a brief contrast agent bolus is administered intravenously during a perfusion CT examination and a number of CT records are generated at defined time intervals. The principle of this examination method consists of the X-ray density of the brain briefly increasing as a result of the bolus-type administration of an intravenous contrast agent. The extent and the time profile of this increase in density, which can be detected in a CT examination, allow conclusions to be drawn about the cerebral perfusion. Parameters which describe the perfusion in the brain are calculated using different mathematical algorithms and methods. These can be illustrated in color-coded parameter images.

The contrast agent is distributed to different extents in the different regions of the brain as a result of the natural differences between gray matter and white matter, and therefore an interpretation of the parameter images which is differentiated according to tissue type is possible. Gray matter combines the regions of the central nervous system which mainly comprise neuron bodies. The totality of nerve fibers form the white matter. In the brain, most parts of the white matter, that is to say in the cerebrum and the cerebellum, are surrounded by the gray matter.

The most important parameters are the cerebral blood flow, the cerebral blood volume and parameters for describing the delay in the contrast agent distribution. The cerebral blood flow forms the basis of the oxygen and nutrient supply for all neurons in the brain. In the case of a healthy adult, approximately 15% of the cardiac output flows through the brain and the surrounding tissue thereof; this corresponds to approximately 700 ml blood per minute. The cerebral blood flow therefore specifies the volume of blood (ml) flowing per mass of tissue (g) per unit time (min). The cerebral blood flow exhibits noticeable regional differences in the brain. In the white matter, the value of the cerebral blood flow is approximately a third of what it is in the gray matter. Due to a lack of energy, the synaptic function of the neurons is disturbed below a certain value and there are failures in the brain. These failures are completely reversible as long as the perfusion normalizes again. However, if the blood flow continues to drop, the structural metabolism in the neurons is also disturbed and there is irreversible damage to the tissue in the case of an extended period of undersupply.

After a stroke, a peripheral edge of only reversibly damaged cerebral matter—the ischemic infarct penumbra—often forms around the irreversibly damaged infarct core; the cells of said penumbra no longer functioning neurologically but not yet being irreversibly damaged. Irreversible damage to the penumbra only occurs once the undersupply lasts. It is for this reason that the therapy after a stroke concentrates on restoring the perfusion in these regions in order to limit the damage to the brain to the greatest possible extent.

The amount of blood located within the brain for supplying the brain and the meninx at a given time is referred to as the cerebral blood volume. Thus, it specifies what volume of blood (ml) can be found per mass of tissue (g). The ratio of the blood volume in the white matter to that in the gray matter is approximately one to two.

Parameters characterizing a perfusion delay within the brain include, for example, the mean transit time and the time a contrast agent bolus requires to reach maximum enrichment in a certain tissue region. This is also called the time until maximum hyperdensity. The mean transit time specifies the amount of time a contrast agent bolus requires to pass through the tissue of interest from a supplying artery and into a venous vessel. Both parameters react very sensitively to variations in the blood supply.

A problem with the previous diagnosis of ischemic cerebral matter lies in the fact that the white matter in the healthy tissue has smaller values of cerebral blood flow and cerebral blood volume than healthy gray matter, just like ischemic regions. It is for this reason that it has not previously been possible for an unambiguous distinction to be made between the healthy white matter and the ischemic cerebral matter belonging to the penumbra. This makes automatic quantitative determination of the penumbra more difficult and the therapy for restoring the perfusion cannot be applied to this region in a targeted fashion.

Thus, it has not previously been possible for a distinction to be made between the types of tissue in a perfusion CT examination, that is to say it has not been possible for the regions undersupplied with blood to be isolated automatically. So as to nevertheless make an evaluation possible, the treating medical practitioner previously marked a region of interest in the anatomically relevant regions of the parameter images. Here, the manual marking of the ischemic region is not always complete and correct; it relies heavily on the experience of the treating medical practitioner; and it is furthermore impeded by the fact that the gray matter and the white matter are strongly intermeshed. Thus, it is practically impossible to differentiate between the white matter and the gray matter, even with the aid of this manual intervention.

SUMMARY

In at least one embodiment of the invention, a method affords the possibility of automatically distinguishing between gray matter and white matter in perfusion CT examination images so the penumbra of an ischemic infarct can be acquired completely and the gray matter can be isolated.

In at least one embodiment, the inventors have recognized that it is possible for the gray matter to be distinguished from the white matter if, starting from the time-dependent image data records from the perfusion CT examination, an automatic segmentation comprising, inter alia, a plurality of histogram analyses with subsequent region growing methods are performed, wherein a logical combination and an exclusion method in respect of the segmented cerebral matter can determine the ischemic gray matter.

In order to perform the segmentation of cerebral tissue, threshold histogram analyses are carried out in the method according to at least one embodiment of the invention. Here, calculating a plurality of three-dimensional images from the time-dependent four-dimensional image data record of the perfusion CT examination in particular is necessary to increase the contrast between gray matter and white matter and to ease distinguishing between them. Moreover, information in respect of the type and the region of the present cerebral matter from the three-dimensional images is linked and so ischemic tissue in the cerebral matter is segmented. Without this novel method, it is not possible for the gray matter to be recognized because the grayscale value of the images on its own does not constitute a sufficient differentiation criterion.

The method according to at least one embodiment of the invention for recognizing white matter and gray matter can in the process be described by the method steps illustrated in the following text. Initially, all image data records recorded with the aid of a perfusion CT examination also comprise, in addition to the cerebral tissue, other regions which are unimportant to the method, e.g. the skull, cerebrospinal fluid spaces and vessels. These are segmented out of the time-dependent image data records for the subsequent steps of the method. It is possible for presently known algorithms, such as e.g. segmentation methods on the basis of thresholds, to be used for this purpose.

Moreover, the image data records of the perfusion CT examination have a time component as a result of the time-dependent spread of the contrast agent. However, the method described herein is not applied to this four-dimensional image data record (x,y,z,t) but to three three-dimensional images (x,y,z) derived therefrom: an average image, a maximum value image and a baseline image.

These time-independent images are already registered to the time-dependent image data record. As a result of this, movements, for example, which can falsify the segmentation results, can be corrected. Without this correction over time, the method according to at least one embodiment of the invention would supply inferior results.

The average image A ("average") specifies the grayscale value, with and without a contrast agent being present, for each pixel averaged over time, and therefore has the advantage that it has less noise than a single record. It can be calculated according to the formula:

$$A(x, y, z) = \frac{1}{N}\sum_{t=t_1}^{t=t_N} I(x, y, z, t),$$

wherein t is the time of the recording, N is the total number of records, that is to say with and without a contrast agent being present, and I is the intensity at the time of the respective recording.

Furthermore, the maximum value image T over time is calculated and it specifies the temporal maximum intensity projection for each pixel during a scanning procedure. The associated formula is:

$$T(x,y,z)=\max I(x,y,z,t).$$

The baseline image B can be calculated in an analogous fashion to the average image A. It likewise specifies the grayscale value for each pixel averaged over time, but only for records without a contrast agent, and it likewise has less noise than a single record. Accordingly, the formula is:

$$B(x, y, z) = \frac{1}{M}\sum_{t=t_1}^{t=t_M} I(x, y, z, t).$$

Here, M is the number of records generated without a contrast agent, t is the time of a recording and I is the intensity at the time of a recording.

In order to obtain a grayscale value difference between pixels of the gray matter and pixels of the white matter which is as large as possible for the region growing method to be performed at the end, a high-contrast image K is calculated and it has a contrast which is as large as possible between regions of the gray matter and regions of the white matter, with the noise in this image at the same time being reduced as much as possible.

To this end, a difference image D can first of all be calculated from the maximum value image T and the average image A by subtracting the average image A from the maximum value image T. A grayscale value range is sought after in the associated histogram of this difference image D which only comprises positive values as a result of the input data from the two images, which grayscale value range describes all pixels which lie within the cerebral tissue, that is to say within the gray matter or white matter. This grayscale value range can for example be determined by empirically determined bounds $D_{min}$ and $D_{max}$ in the histogram. Using these bounds, a maximum grayscale value which lies within these bounds can be determined. Subsequently, it is expedient to normalize the difference image D for the value range from zero to one in the histogram by dividing all grayscale values of the difference image D by the greatest grayscale value found such that a better comparability between the images is achieved. This generates a normalized difference image D*.

Subsequently, the sought after high-contrast image K can be composed from the pixels of the average image A, the maximum value image T and the normalized difference image D*. Herein, all pixels whose grayscale values in the normalized difference image D* lie below the minimum threshold $D_{min}$ originate from the average image A and all pixels whose grayscale values lie above the maximum threshold $D_{max}$ originate from the maximum value image T. All other pixels can be added in a weighted fashion. The corresponding formula is:

$$K(x, y, z) = \begin{cases} D^*(x, y, z) \leq D_{min}; & A(x, y, z) \\ D^*(x, y, z) \geq D_{max}; & T(x, y, z) \\ \text{otherwise}; & [T(x, y, z) \cdot D^*(x, y, z)] + [A(x, y, z) \cdot (1 - D^*(x, y, z))] \end{cases}.$$

Next, a histogram analysis of the high-contrast image K is performed in order to be able to find image regions whose grayscale values correspond to the grayscale values of the sought after gray matter or white matter. In the process, the assumption is made that only one half of the brain of the patient is affected by an ischemic stroke and so only the health hemisphere of the brain is used for this threshold histogram analysis.

Although there are two types of cerebral tissue, namely gray matter and white matter, which should theoretically differ in their grayscale values as a result of their differing cerebral blood flow—white matter is less perfused than gray matter—the histogram distribution of the grayscale values is assumed to be a unimodal Gaussian distribution. The reason for this is that the grayscale values of these regions lie very close to one another and they can therefore hardly be separated. In order to determine the required thresholds for limiting the grayscale value range, characteristic parameters of this distribution, for example the maximum value and the standard deviation, are firstly determined by an approximation, for example by the "maximum likelihood" method. Starting from these parameters, a lower and an upper threshold can then be calculated, with the sought after thresholds respectively being determined by the standard deviation above and below the maximum value of the distribution.

Accordingly, pixels whose grayscale values lie below the lower threshold are in the healthy white matter and pixels whose grayscale values lie above the upper threshold are in the healthy gray matter. Hence a first distinction has been made in the healthy hemisphere between image regions which consist of gray matter or white matter.

However, since the grayscale values in the ischemic regions of the gray matter are less than those in the healthy gray matter, this threshold histogram analysis of the damaged hemisphere will falsely classify pixels from the ischemic gray matter as white matter. To nevertheless find regions with ischemic gray matter, it is expedient to resort to the difference image D. A threshold histogram analysis is performed in turn; however, only one threshold corresponding to the average grayscale value in the histogram is determined. All pixels whose grayscale values lie below the average grayscale value are located in a region in which both healthy white matter and ischemic gray matter can occur. As a result of the perfusion not being as strong, these pixels have, compared to the remaining cerebral tissue, only experienced a small increase in their grayscale values as a result of the contrast agent.

Regions of the overall gray matter can be limited further using the just determined white region and ischemic gray region. To this end, a further histogram analysis is effected. However, the source in this case is the baseline image B because this comprises time-averaged records which do not include a contrast agent. Thus, this image is particularly suitable because it is independent of the perfusion conditions and so the healthy gray matter and the ischemic gray matter are imaged with the same grayscale values and differ from their surroundings. The same analysis as was already described above for the high-contrast image K is performed for the baseline image B; however, in this case the difference is that both hemispheres are considered. However, since the object only includes the pixels from regions of the gray matter, it is only a lower threshold for the grayscale values that is found. The grayscale values of the sought after pixels then lie above this threshold.

Since the entire brain and not, as previously, only the healthy hemisphere was used for the analysis, the threshold can be sought after closer to the average grayscale value of the normal distribution. That is to say the grayscale value range can be taken to be that broad that it also includes the image regions in which ischemic gray matter is present which is already starting to decompose as a result of insufficient perfusion and as a result of which the grayscale value thereof is even smaller.

In order to now recognize the image regions in which only ischemic gray matter is present, a logical combination can be undertaken by applying an AND operator on the grayscale value range determined from the normalized difference image D*, which comprises both healthy white matter and ischemic gray matter, and the grayscale value range determined from the baseline image B, which comprises both healthy gray matter and ischemic gray matter; and by using the condition that ischemic gray matter can only be found in the damaged hemisphere.

When classified correctly, the resultant pixels have the following properties: they lie in the damaged hemisphere, are located in the gray matter and have below-average perfusion, that is to say they are ischemic.

Thus, grayscale value ranges with healthy white matter, healthy gray matter and ischemic gray matter are characterized after this sequence of threshold histogram analyses. Before the region growing method can be performed, it is expedient to still mark respective seed points in these three regions.

The region growing method can now be performed three times per recorded image, that is to say respectively once for the seed points in healthy gray matter, in healthy white matter and in ischemic gray matter. In the process, different types of termination criteria for the growth can be used. By way of example, each image has a static upper and lower boundary for the grayscale value range in which the respective seed point is, and a dynamic boundary which can be calculated from the surroundings of the seed point.

The static boundaries can be obtained by empirical tests. They respectively specify the maximum grayscale deviation in respect of the mean value of the estimated normal distribution of the high-contrast image K. It is possible for an e.g. 31×31 pixel region in the x- and y-directions, that is to say in an image with the seed point as its center, to be defined for the dynamic boundary. By way of example, the arithmetic mean of the grayscale values of the already classified pixels can now be calculated in this region. The difference between this value and the grayscale value of the seed point expediently does not exceed a likewise empirically determined value. A fixed boundary of the grayscale value range of the ischemic cerebral matter cannot be determined because the perfusion conditions can change continuously. It is for this reason that it is better if only the dynamic boundary as a function of its surroundings is used for this region.

The region growing method now results in there being three image regions for the three different tissue types of the brain. In order to compensate for effects such as the partial volume effect and an imprecise segmentation of the cerebrospinal fluid spaces, additional points which lie on the brain contour are added to the gray matter. Here, the brain contour is considered to be the shape of the cerebral matter which describes the pia mater. This is performed for a strip approximately one centimeter wide which, based on anatomical discoveries, can always be assumed to consist of gray matter. The reason for this extension is that it is possible for the method according to at least one embodiment of the invention to falsely classify voxels as white matter in the edge region. Hence, knowledge of anatomy that white matter cannot actually be located in this region can be used at this stage. If the algorithm of the method according to at least one embodiment of the invention has erred, the segmentation result is thus corrected at this location.

Finally, the three image regions can be linked to form the final resultant image region of the gray matter according to the following procedure: all regions which arise as healthy gray matter or ischemic gray matter from the region growing method, or which are not contained in any of the previously determined regions, can be classified and grouped as gray matter. This linking ensures that erroneous classifications always lead to an over-segmentation of the gray matter. As a result of this, no ischemic regions, the grayscale values of which being similar to the white matter, are excluded from the region of the infarct penumbra. Regions are only classified as white matter if they only occur in the result of the region growing method for the white matter.

Furthermore, at least one embodiment of the invention relates to a CT system with a control and computational unit, in which programs or program modules are stored, which can execute the method according to at least one embodiment of the invention.

In accordance with this basic idea, the inventors propose a method for distinguishing between gray matter and white matter starting from a time-dependent computed tomography image data record from a perfusion CT examination, wherein a plurality of time-independent images are calculated from the time-dependent image data record, a plurality of threshold histogram analyses are performed in order to determine regions of the brain which can be assigned to one or more types of cerebral matter, and subsequently the region of gray matter is determined from the information obtained in respect of type and region of the cerebral matter using at least one logical combination and at least one exclusion method.

In the process, it is very expedient for the time-independent images to be registered to the time-dependent image data record. This can eliminate movements of the patient. In the process, a rigid registration, comprising a translation and a rotation, is particularly suitable. It goes without saying that the further calculations are effected on the basis of the registered images.

The method according to at least one embodiment of the invention can advantageously comprise the following method steps:

defining a work region in the time-dependent image data record which only comprises cerebral matter, that is to say gray matter, white matter and ischemic gray matter, with all further steps being performed in this work region;

calculating the following three-dimensional image data records from the time-dependent image data record:
an average image with and without a contrast agent being present,
a maximum value image over time, and
a baseline image without a contrast agent being present;

determining a difference image from the average image and the maximum value image;

determining a normalized difference image from the image data of the difference image;

generating a high-contrast image with increased contrast between white matter and gray matter from the average image, the maximum value image and the normalized difference image;

determining a first grayscale value range which only comprises gray matter and a second grayscale value range which only comprises white matter by threshold histogram analysis of the high-contrast image, wherein only the image data of the undamaged hemisphere is considered;

determining a third grayscale value range which comprises both healthy white matter and ischemic gray matter by threshold histogram analysis of the normalized difference image;

determining a fourth grayscale value range which comprises both healthy gray matter and ischemic gray matter by threshold histogram analysis of the baseline image;

generating a fifth grayscale value range which lies in the damaged hemisphere and only comprises ischemic gray matter by a logical combination of the third grayscale value range and the fourth grayscale value range;

determining seed points for respectively the first grayscale value range, the second grayscale value range and the fifth grayscale value range;

performing a region growing method respectively starting at the previously determined seed points and generating a first image region, a second image region, and a fifth image region;

generating an expanded first image region by adding cerebral regions which constitute anatomically assured gray matter to the first image region; and determining a resultant image region which comprises both healthy gray matter and ischemic gray matter and all regions of the brain which have not yet been acquired by means of a logical combination of the changed first image region, the second image region and the fifth image region.

A region which, starting from the pia mater, reaches one centimeter into the cerebral matter is advantageously used as the anatomically assured gray matter. As it were, the leptomeninx describes the contour of the cerebral matter with all folds. This expansion can correct erroneous segmentation results.

The time component is advantageously eliminated when calculating the three-dimensional image data records from the time-dependent image data record from the perfusion CT examination. The following formula can be used for generating the average image, with all records being taking into account:

$$A(x, y, z) = \frac{1}{N} \sum_{t=t_1}^{t=t_N} I(x, y, z, t).$$

The maximum value image can be determined using the following formula:

$$T(x,y,z) = \max I(x,y,z,t).$$

Advantageously, the baseline image can be determined in an analogous fashion to the average image; however, only records without contrast agent are taken into account. The associated formula is:

$$B(x, y, z) = \frac{1}{M} \sum_{t=t_1}^{t=t_M} I(x, y, z, t).$$

In all formulae, t respectively is the time of a recording, N or M refers to the number of records with and without, or only without, the contrast agent and I is the intensity of the respective recording.

In the further course of the method according to at least one embodiment of the invention, further images can advantageously be generated from the image data of the average image and the maximum value image. These are the difference image and, following therefrom, the high-contrast image.

The difference image is preferably generated by the image data of the average image being subtracted from the image data of the maximum value image. The difference image then only comprises positive image data. Furthermore, a threshold histogram analysis of the difference image can be performed in which a grayscale value range with a lower and an upper limiting threshold is determined, with a maximum grayscale value being located in the center thereof. In the process, the grayscale values outside of this grayscale value range describe portions of the gray matter and the white matter in the healthy hemisphere.

Subsequently, the difference image can be normalized by advantageously dividing the grayscale values by the previously determined maximum grayscale value and thus a normalized difference image is created. The high-contrast image can be determined using this normalized difference image, the image data of the average image and of the maximum value image. The formula advantageously used for this is:

$$K(x, y, z) = \begin{cases} D^*(x, y, z) \le D_{min}; & A(x, y, z) \\ D^*(x, y, z) \ge D_{max}; & T(x, y, z) \\ \text{otherwise}; & [T(x, y, z) \cdot D^*(x, y, z)] + [A(x, y, z) \cdot (1 - D^*(x, y, z))] \end{cases}$$

wherein $D_{min}$ and $D_{max}$ constitute the lower and the upper threshold of the previously determined grayscale value range in the difference image.

In the process, all pixels in the high-contrast image whose corresponding pixels in the normalized difference image have grayscale values which lie below the lower threshold can be taken from the average image. And all pixels whose corresponding pixels have grayscale values which lie above the upper threshold can be taken from the maximum value image. According to at least one embodiment of the invention, all other pixels can be combined by the weighted addition described in the formula.

Advantageously, the threshold histogram analysis in order to determine the first and the second grayscale value range, applied in the next step of the method according to at least one embodiment of the invention, is performed under the assumption that the histogram approximately corresponds to a unimodal Gaussian distribution. The characterizing parameters of this approximate Gaussian distribution—preferably the maximum value and the standard deviation—can advantageously be determined by, for example, applying a maximum likelihood method.

An upper and a lower threshold can then advantageously be determined from these parameters, wherein the image data of the first grayscale value range lies above the upper threshold and the image data of the second grayscale value range lies below the lower threshold.

Furthermore, it is advantageous for only one threshold, which corresponds to an average grayscale value of the histogram, to be used in the threshold histogram analysis in order to determine the third grayscale value range, wherein the image data of the third grayscale value range lies below the threshold.

The threshold histogram analysis in order to determine the fourth grayscale value range can be performed in an analogous fashion to the threshold histogram analysis in order to determine the first and the second grayscale value range. Advantageously, the assumption can also be made in this case that the histogram of the baseline image corresponds to a unimodal Gaussian distribution. The parameters of this approximate Gaussian distribution—preferably the maximum value and the standard deviation—can likewise be determined in an advantageous fashion using a maximum likelihood method. However, in this case it is preferably only an upper threshold which is determined from the parameters, with the image data of the fourth grayscale value range lying above this threshold.

In the case of the logical combination performed in order to generate the fifth grayscale value range which characterizes the ischemic gray matter in the further course of the method according to at least one embodiment of the invention, a logical AND operator can advantageously be utilized.

It is advantageously possible for two different termination criteria, a static termination criterion and a dynamic termination criterion, to be used in the region growing method performed according to the invention. The static boundaries of the static termination criterion can for example be determined empirically and the dynamic boundaries of the dynamic criterion can for example be determined from the arithmetic mean of a grayscale value distribution within a predetermined region. Advantageously it is only the dynamic termination criterion that is used for the region growing method of the fifth grayscale value range, that is to say the region with the ischemic gray matter, because there is no fixed static boundary for the grayscale value. The resultant image region can advantageously be determined by an exclusion method with a logical exclusion operator A. This operator groups together all regions to the resultant region which were determined to be healthy gray matter or ischemic gray matter or which were not considered until now, that is to say which do not occur in any of the regions. Expressed mathematically, this corresponds to the formula:

$$A = RG_{ig} + RG^*_{gg} + R_G \text{ with } R_G = G - \lfloor RG_{ig} + RG^*_{gg} + RG_{gw} \rfloor.$$

Here, G represents the entire cerebral tissue and $R_G$ represents all regions of the cerebral tissue not acquired previously.

Normally, this means that the resultant image region then also comprises image regions which belong neither to the expanded first grayscale value range nor to the second grayscale value range or the fifth grayscale value range. This can ensure that regions classified incorrectly or not at all are not excluded but are always assigned to the gray matter with the ischemic infarct penumbra.

Moreover, the invention relates to a control and computational unit with a storage medium in which a computer program or program module is stored, which can execute the vessel recognition method according to at least one embodiment of the invention.

BRIEF DESCRIPTION OF THE DRAWINGS

In the following text, the invention will be described in more detail on the basis of an example embodiment with the aid of the figures, with reference being made to the fact that only those elements essential to the intuitive understanding of the invention are shown. In the process, the following reference signs are used: 1b: threshold histogram analysis of the baseline image; 1d: threshold histogram analysis of the normalized difference image; 1k: threshold histogram analysis of the high-contrast image; A: average image; C1: CT system; C2: first X-ray tube; C3: first detector; C4: second X-ray tube (optional); C5: second detector (optional); C6: gantry housing; C7: patient; C8: displaceable patient couch; C9: system axis; C10: control and computational unit; C11: contrast agent administration device; B: baseline image; D: difference image; D*: normalized difference image; G: cerebral tissue; K: high-contrast image; $Prg_1$ to $Prg_n$: computer program or program module; $RG_{gg}$: result of the region growing method for healthy gray matter; $RG_{gg}$*: expanded result of the region growing method for healthy gray matter; $RG_{gw}$: result of the region growing method for healthy white matter; $RG_{ig}$: result of the region growing method for ischemic gray matter; $R_g$: remaining cerebral matter; T: maximum value image; gg: grayscale value range of the healthy gray matter; gw: grayscale value range of the healthy white matter; ig: grayscale value range of the ischemic gray matter; (x,y,z): time-independent image data record; (x,y,z,t): time-dependent image data record; A: logical operator of the exclusion method; ^: logical AND operator.

In detail.

DETAILED DESCRIPTION OF THE EXAMPLE EMBODIMENTS

Figure 1:
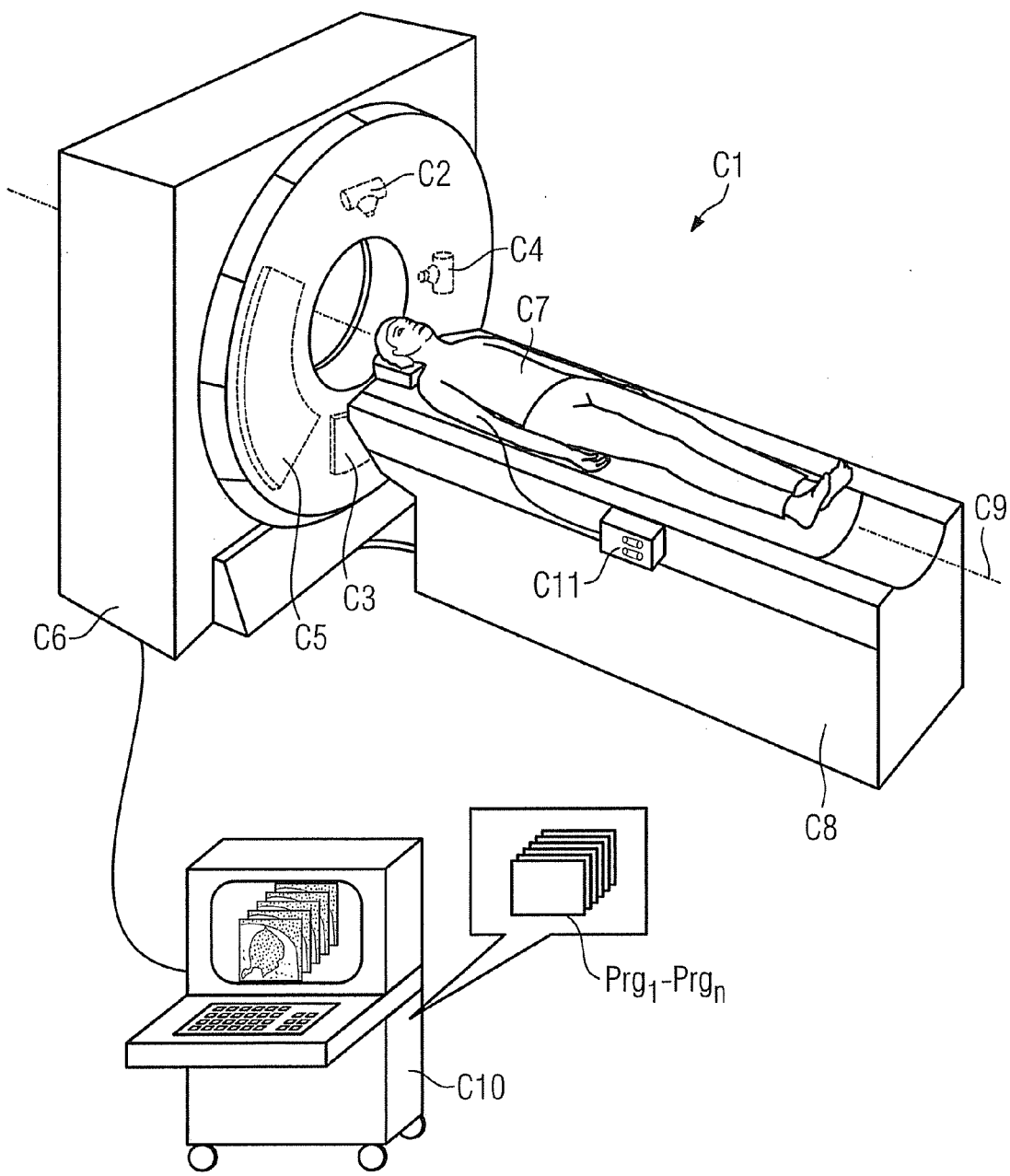
FIG. 1 shows a schematic illustration of a CT system for performing a perfusion CT examination.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements' present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

FIG. 1 illustrates, in an example fashion, a computed tomography system C1 with a detector C3 for performing a perfusion CT examination. This CT system C1 has a gantry housing C6, in which a gantry with an X-ray tube C2 is located, which rotates about a system axis C9 together with a detector C3 lying opposite the X-ray tube C2. Optionally, it is possible for at least one second X-ray tube C4 and a detector C5 lying opposite to the latter to be arranged on the gantry. Depending on the type of scan, this can increase the scanning rate or a different type of scan, for example a phase-contrast scan can be obtained. For the purposes of scanning, a patient C7, for example, lying on a patient couch C8 is pushed through the measuring field while the X-ray tubes C2 and C4 and the detectors C3 and C5 rotate around the system axis C9 on the gantry.

Using a contrast agent administration device C11, a contrast agent bolus can be intravenously administered to the patient C7 in order to be able to assess the blood flow in the brain, for example after an ischemic infarct. At the same time, multiple CT records with a certain scan duration are generated at defined time intervals. The signals detected by the detector C3 can then be processed directly using detector electronics in a central computational and control unit C10. Computer programs $Prg_1$-$Prg_n$, which can execute the method according to an embodiment of the invention, can also be stored therein.

Figure 2:
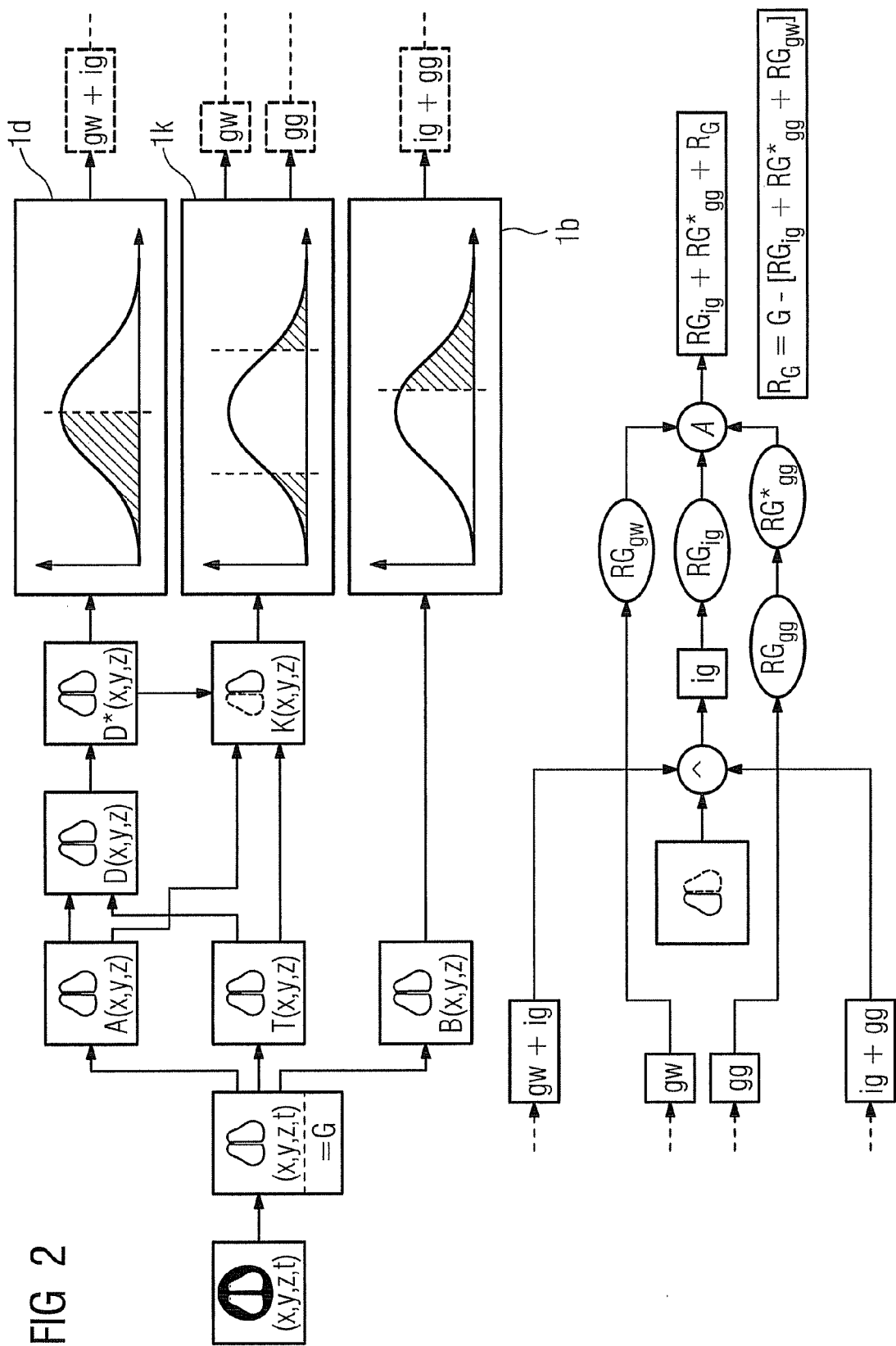
FIG. 2 shows a flowchart of the method according to an embodiment of the invention.

FIG. 2 shows a flowchart of the method according to an embodiment of the invention for distinguishing between gray matter and white matter on the basis of perfusion CT image data records. For improved clarity, this diagram was subdivided into an upper and a lower part.

First of all, image regions which do not belong to the cerebral tissue, e.g. the skull, vessels and cerebrospinal fluid spaces, are removed from the time-dependent image data records (x,y,z,t) of a perfusion CT examination of the brain which specifies the perfusion in the brain. Time-independent image data records (x,y,z) are required for performing the further method steps and these can be derived from the time-dependent image data record (x,y,z,t). In the process, it is important for the time-independent images (x,y,z) to be registered to the time-dependent (x,y,z,t) image data record in order to compensate for artifacts. These images are the average image A, the baseline image B and the maximum value image T. Pixels whose grayscale values were averaged over time are combined in the so-called average image A(x,y,z). The baseline image B(x,y,z) is generated in an analogous fashion, with only records without a contrast agent being considered in this case. The maximum grayscale value over the entire time is selected for each pixel in the maximum value image T(x,y,z).

Two further images are generated from the image data of these three images: the difference image D and the high-contrast image K. The difference image D is calculated according to the formula T(x,y,z)−A(x,y,z) and therefore only comprises positive values. It is subsequently normalized. The high-contrast image K(x,y,z) is determined from the image data of this normalized difference image D*(x,y,z) and the image data T(x,y,z) and A(x,y,z) of the maximum value image T and the average image A. In said high-contrast image K, regions with gray matter and regions with white matter have a contrast difference which is as large as possible.

Now the various threshold value histogram analyses 1b, 1k and 1d of the baseline image B, the high-contrast image K and the normalized difference image D* are performed. They are ultimately used to determine a grayscale value range, or the image region associated therewith, which can be assigned to the healthy gray matter, the healthy white matter or the ischemic gray matter. A grayscale value range (gw+ig) in which both healthy white matter and ischemic gray matter occur is determined from the normalized difference image D*. These cerebral matters have very similar grayscale values since both types of tissue are poorly perfused. In the threshold histogram analysis 1k of the high-contrast image K, it is only grayscale value ranges of the healthy cerebral matter that is sought after. Thus, only the healthy hemisphere of the brain is considered for this purpose. A grayscale value range gg, in which only health gray matter occurs, and a grayscale value range gw, in which only healthy white matter occurs, are obtained therefrom. The threshold histogram analysis 1b of the baseline image B results in a grayscale value range (ig+gg) which comprises both ischemic gray matter and healthy gray matter.

Thus, up until now, four different grayscale value ranges were determined: a grayscale value range gg, a grayscale value range gw, a grayscale value range (gw+ig) and a grayscale value range (gg+ig). At this point, the transition from the upper part of the flowchart to the lower part of the flowchart takes place.

A further grayscale value range ig can be determined, using a logical AND combination ^, from the grayscale value ranges (gw+ig) and (gg+ig), and from the assumption that the ischemic cerebral matter can only be found in the damaged hemisphere, the range being located in the gray matter of the damaged hemisphere and having a below-average perfusion. For the further method, only the grayscale values gg, gw and ig are of importance.

Before respective seed points for these grayscale value ranges are determined in the next step, the healthy gray region is expanded to the grayscale value range gg* by an approximately one centimeter wide strip along the brain contour described by the pia mater which can, in an anatomically assured fashion, be assumed to also consist of gray matter.

Then the seed points are determined in the three grayscale value ranges or the associated image regions. A region growing method is applied in each case starting from the seed points. The results of the region growing methods $RG^*_{gg}$, $RG_{gw}$ and $RG_{ig}$ are logically combined with one another in the final step to form the sought after image region. The exclusion operator A used for this purpose has the form:

$$A = RG_{ig} + RG^*_{gg} + R_G \text{ with } R_G = G - \lfloor RG_{ig} + RG^*_{gg} + RG_{gw} \rfloor,$$

wherein G represents the entire cerebral tissue and $R_G$ describes that part of the brain which was assigned to neither the healthy gray grayscale value range gg* nor the healthy white grayscale value range gw or the ischemic gray grayscale value range ig. That is to say this is cerebral matter which was not previously acquired and it is automatically assigned to the resultant region to exclude the possibility of erroneous classifications.

Thus, the sought after resultant region ($RG_{ig}$+$RG^*_{gg}$+$R_G$) comprises the entire gray matter and, just to be sure, all regions $R_G$ which were not acquired.

It goes without saying that the abovementioned features of the invention can be used not only in the respectively specified combination but also in other combinations or on their own, without departing from the scope of the invention.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, computer readable medium and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable medium and is adapted to perform any one of the aforementioned methods when run on a computer device (a device including a processor). Thus, the storage medium or computer readable medium, is adapted to store information and is adapted to interact with a data processing facility or computer device to execute the program of any of the above mentioned embodiments and/or to perform the method of any of the above mentioned embodiments.

The computer readable medium or storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for determining a region of gray matter in a brain starting from a time-dependent computed tomography image data record from a perfusion CT examination, the method comprising:
    defining a work region in the time-dependent computed tomography image data record which only comprises healthy gray matter, healthy white matter and ischemic gray matter;
    calculating a plurality of three-dimensional time-independent images from the time-dependent computed tomography image data record, the plurality of three-dimensional time-independent images including an average image with and without a contrast agent being present, a maximum value image over time and a baseline image without a contrast agent being present;
    determining a normalized difference image from the image data of a difference image, the difference image being determined from the average image and the maximum value image;
    generating a high-contrast image with increased contrast between white matter and gray matter from the average image, the maximum value image and the normalized difference image;
    determining a first grayscale value range, which only comprises gray matter, and a second grayscale value range, which only comprises white matter, by threshold histogram analysis of the high-contrast image, wherein only the image data of an undamaged hemisphere of the brain is considered;
    determining a third grayscale value range which comprises both the healthy white matter and the ischemic gray matter by threshold histogram analysis of the normalized difference image;
    determining a fourth grayscale value range which comprises both the healthy gray matter and the ischemic gray matter by threshold histogram analysis of the baseline image;
    generating a fifth grayscale value range which lies in the damaged hemisphere and only comprises the ischemic gray matter by a logical combination of the third grayscale value range and the fourth grayscale value range;
    determining seed points for respectively the first grayscale value range, the second grayscale value range and the fifth grayscale value range;
    performing a region growing method respectively starting at the previously determined seed points and generating a first image region, a second image region, and a fifth image region;
    generating an expanded first image region by adding cerebral regions which constitute anatomically assured gray matter to the first image region; and
    determining a resultant image region which comprises both the healthy gray matter and the ischemic gray matter and all regions of the brain which have not yet been acquired by way of a logical combination of the changed first image region, the second image region and the fifth image region.

2. The method as claimed in claim 1, wherein the time-independent images are registered to the time-dependent computed tomography image data record.

3. The method as claimed in claim 1, wherein a region which, starting from a pia mater, reaches one centimeter into the cerebral matter is used as the anatomically assured gray matter.

4. The method as claimed in claim 1, wherein a formula is used to calculate the average image A, the formula being:

$$A(x, y, z) = \frac{1}{N} \sum_{t=t_1}^{t=t_N} I(x, y, z, t),$$

wherein t is a time of a recording, N is a total number of records and I is an intensity at the time of the respective recording.

5. The method as claimed in claim 1, wherein a formula is used to calculate the maximum value image T, the formula being:

$$T(x,y,z) = \max I(x,y,z,t),$$

wherein t is a time of a recording and I is an intensity at the time of the respective recording.

6. The method as claimed in claim 1, wherein a formula is used to calculate the baseline image B, the formula being:

$$B(x, y, z) = \frac{1}{M} \sum_{t=t_1}^{t=t_M} I(x, y, z, t),$$

wherein t is a time of the recording, M is a number of records without the contrast agent and I is an intensity at the time of the respective recording.

7. The method as claimed in claim 1, wherein the image data of the average image is subtracted from the image data of the maximum value image in order to determine the difference image.

8. The method as claimed in claim 1, wherein a lower bound and an upper bound as well as an average maximum grayscale value are determined in the difference image.

9. The method as claimed in claim 8, wherein the grayscale values are divided by the previously determined average maximum grayscale value in order to normalize the difference image.

10. The method as claimed in claim 1, wherein a formula is used to generate the high-contrast image K, the formula being:

$$K(x, y, z) = \begin{cases} D*(x, y, z) \leq D_{min}; & A(x, y, z) \\ D*(x, y, z) \geq D_{max}; & T(x, y, z) \\ \text{otherwise}; & [T(x, y, z) \cdot D*(x, y, z)] + [A(x, y, z) \cdot (1 - D*(x, y, z))] \end{cases}$$

11. The method as claimed in claim 1, wherein the threshold histogram analysis in order to determine the first and the second grayscale value range is performed under an assumption that the histogram corresponds to a unimodal Gaussian distribution.

12. The method as claimed in claim 11, wherein a maximum likelihood method is applied in order to determine parameters of the unimodal Gaussian distribution.

13. The method as claimed in claim 12, wherein an upper and a lower threshold are determined starting from the parameters, and
the image data lies above the upper threshold within the first grayscale value range and the image data lies below the lower threshold within the second grayscale value range.

14. The method as claimed in claim 12, wherein the parameters of the unimodal Gaussian distribution include the maximum value and a standard deviation.

15. The method as claimed in claim 1, wherein only one threshold which corresponds to an average grayscale value of the histogram is used in the threshold histogram analysis in order to determine the third grayscale value range, and
the image data lies below the threshold within the third grayscale value range.

16. The method as claimed in claim 1, wherein the threshold histogram analysis, in order to determine the fourth grayscale value range, is performed under an assumption that the histogram corresponds to a unimodal Gaussian distribution.

17. The method as claimed in claim 16, wherein a maximum likelihood method is applied in order to determine parameters of the unimodal Gaussian distribution.

18. The method as claimed in claim 17, wherein an upper threshold is determined starting from the parameters, and
the image data of the fourth image region lies above the threshold.

19. The method as claimed in claim 17 wherein the parameters of the unimodal Gaussian distribution include the maximum value and a standard deviation.

20. The method as claimed in claim 1, wherein a logical AND operator is utilized in the logical combination for extracting the fifth grayscale value range.

21. The method as claimed in claim 1, wherein two different termination criteria are used in the region growing method.

22. The method as claimed in claim 21, wherein a static termination criterion is used.

23. The method as claimed in claim 21, wherein a dynamic termination criterion is used.

24. The method as claimed in claim 23, wherein the dynamic termination criterion is used in the region growing method in order to generate the fifth image region.

25. The method as claimed in claim 1, wherein the resultant image region is determined using an exclusion operator.

26. The method as claimed in claim 25, wherein the exclusion operator corresponds to a formula:

$$A = RG_{ig} + RG^*_{gg} + R_G \text{ with } R_G = G - \lfloor RG_{ig} + RG^*_{gg} + RG_{gw} \rfloor,$$

wherein G corresponds to an entire cerebral tissue and $R_G$ corresponds to all regions of the brain that have not previously been acquired.

27. A control and computational unit for determining a region of gray matter in a brain starting from a time-dependent computed tomography image data record from a perfusion CT examination, the unit comprising:
a processor configured to
define a work region in the time-dependent computed tomography image data record which only comprises healthy gray matter, healthy white matter and ischemic gray matter;
calculate a plurality of three-dimensional time-independent images from the time-dependent computed tomography image data record, the plurality of three-dimensional time-independent images including an average image with and without a contrast agent being present, a maximum value image over time and a baseline image without a contrast agent being present;
determine a normalized difference image from the image data of a difference image, the difference image being determined from the average image and the maximum value image;
generate a high-contrast image with increased contrast between white matter and gray matter from the average image, the maximum value image and the normalized difference image;
determine a first grayscale value range, which only comprises gray matter, and a second grayscale value range, which only comprises white matter, by threshold histogram analysis of the high-contrast image, wherein only the image data of an undamaged hemisphere of the brain is considered;

determine a third grayscale value range which comprises both the healthy white matter and the ischemic gray matter by threshold histogram analysis of the normalized difference image;

determine a fourth grayscale value range which comprises both the healthy gray matter and the ischemic gray matter by threshold histogram analysis of the baseline image;

generate a fifth grayscale value range which lies in the damaged hemisphere and only comprises the ischemic gray matter by a logical combination of the third grayscale value range and the fourth grayscale value range;

determine seed points for respectively the first grayscale value range, the second grayscale value range and the fifth grayscale value range;

perform a region growing method respectively starting at the previously determined seed points and generating a first image region, a second image region, and a fifth image region;

generate an expanded first image region by adding cerebral regions which constitute anatomically assured gray matter to the first image region; and determine a resultant image region which comprises both the healthy gray matter and the ischemic gray matter and all regions of the brain which have not yet been acquired by way of a logical combination of the changed first image region, the second image region and the fifth image region.

28. A computer readable medium including a computer program product, the computer program product comprising instructions, which when executed on a computer device, causes the computer device to perform functions for determining a region of gray matter in a brain starting from a time-dependent computed tomography image data record from a perfusion CT examination, the functions including:

defining a work region in the time-dependent computed tomography image data record which only comprises healthy gray matter, healthy white matter and ischemic gray matter;

calculating a plurality of three-dimensional time-independent images from the time-dependent computed tomography image data record, the plurality of three-dimensional time-independent images including an average image with and without a contrast agent being present, a maximum value image over time and a baseline image without a contrast agent being present;

determining a normalized difference image from the image data of a difference image, the difference image being determined from the average image and the maximum value image;

generating a high-contrast image with increased contrast between white matter and gray matter from the average image, the maximum value image and the normalized difference image;

determining a first grayscale value range, which only comprises gray matter, and a second grayscale value range, which only comprises white matter, by threshold histogram analysis of the high-contrast image, wherein only the image data of an undamaged hemisphere of the brain is considered;

determining a third grayscale value range which comprises both the healthy white matter and the ischemic gray matter by threshold histogram analysis of the normalized difference image;

determining a fourth grayscale value range which comprises both the healthy gray matter and the ischemic gray matter by threshold histogram analysis of the baseline image;

generating a fifth grayscale value range which lies in the damaged hemisphere and only comprises the ischemic gray matter by a logical combination of the third grayscale value range and the fourth grayscale value range;

determining seed points for respectively the first grayscale value range, the second grayscale value range and the fifth grayscale value range, performing a region growing method respectively starting at the previously determined seed points and generating a first image region, a second image region, and a fifth image region;

generating an expanded first image region by adding cerebral regions which constitute anatomically assured gray matter to the first image region; and determining a resultant image region which comprises both healthy gray matter and ischemic gray matter and all regions of the brain which have not yet been acquired by way of a logical combination of the changed first image region, the second image region and the fifth image region.

* * * * *